(12) United States Patent
Wohrle

(10) Patent No.: US 6,783,117 B2
(45) Date of Patent: Aug. 31, 2004

(54) SCENT DELIVERY SYSTEM

(76) Inventor: Gregory D. Wohrle, 1110 Cherry Palm La., Hollywood, FL (US) 33019

( * ) Notice: Subject to any disclaimer, the term of this patent is extended or adjusted under 35 U.S.C. 154(b) by 0 days.

(21) Appl. No.: 10/176,129

(22) Filed: Jun. 20, 2002

(65) Prior Publication Data

US 2002/0158351 A1 Oct. 31, 2002

Related U.S. Application Data

(63) Continuation-in-part of application No. 09/902,307, filed on Jul. 10, 2001, now Pat. No. 6,619,559.
(60) Provisional application No. 60/217,161, filed on Jul. 10, 2000, now abandoned.

(51) Int. Cl.$^7$ ................................................ B01F 3/04
(52) U.S. Cl. ...................... 261/26; 261/104; 261/142; 261/DIG. 65; 261/DIG. 88; 261/DIG. 89; 422/124
(58) Field of Search .................. 261/26, 104, 142, 261/DIG. 65, DIG. 88, DIG. 89; 422/124

(56) References Cited

U.S. PATENT DOCUMENTS 2,867,866 A * 1/1959 Steele ........................ 422/124
4,629,604 A * 12/1986 Spector ...................... 422/124

* cited by examiner

*Primary Examiner*—Robert A. Hopkins
(74) *Attorney, Agent, or Firm*—Gold & Rizvi, P.A.; Glenn E. Gold; H. John Rizvi

(57) ABSTRACT

A scent-emitting system includes a plurality of cartridges containing scented fluids and seated within pockets formed in a system tray. Heating members are provided for heating the cartridges to encourage the formation of scented vapors and an actuation subassembly is provided for selectively actuating the scent cartridges to release the scented vapors. An internal fan generates an air flow for communicating the scented vapors through housing vent openings to an external environment.

42 Claims, 16 Drawing Sheets

SCENT DELIVERY SYSTEM

CROSS REFERENCE TO RELATED APPLICATION

This application is a continuation-in-part of application Ser. No. 09/902,307 filed on Jul. 10, 2001, now U.S. Pat. No. 6,619,559 which claims the priority of provisional Application No. 60/217,161 filed on Jul. 10, 2000, now abandoned.

BACKGROUND OF THE INVENTION

1. Field of the Invention

The present invention relates generally to scent emitting devices, and more particularly to an electric/electronic scent diffusing system.

2. Description of the Prior Art

It is well known to use deodorizers, air fresheners, candles, plug-ins and the like, to provide a desired scent or aroma in a home, office or other such environment. In fact, many people place air fresheners in rooms to conceal existing undesirable odors, or merely to make the air more fragrant. Various types of air freshening devices are commercially available. Most such commercial air freshening devices provide for a predetermined single scent, and little or no means for controlling the strength, duration, coverage area and other characteristics of the emitted scent.

Some air fresheners that allow a user to selectively alter the scent delivered by a device have been described. For example, U.S. Pat. No. 5,695,692 to Kennedy and U.S. Pat. No. 5,178,327 to Palamand disclose air freshening units including a container which carries a cartridge having a plurality of segments, or sections, each having a solid material impregnated with a scented substance. In each case, the cartridge can be manually rotated to position a particular segment having a desired scent into alignment with an opening in the container to facilitate emission of the desired scent into the surrounding environment.

U.S. Pat. No. 2,103,609 to Bradburn discloses an air freshener having a body carrying a plurality of open-topped vials of scented substances. A rotatable cover is mounted on the body to close and seal the vials. The cover has an opening that can be selectively aligned with any one of the vials in order to enable the substance contained within the vial to evaporate into the air.

The aforementioned air fresheners share a number of disadvantages and limitations. For instance, each of the disclosed air fresheners must be manually manipulated to alter the type of scent. Additionally, none of the disclosed air fresheners provide means for controlling the strength, duration or coverage area of the emitted scent. Furthermore, the disclosed air fresheners are provided in containers that would be unsightly positioned, for example, in a high-end home entertainment unit.

Electronic aroma generating devices and systems providing for more controlled scent emission have been described. For example, U.S. Pat. No. 5,591,409 to Watkins discloses an apparatus for introducing precisely controlled amounts of aromatic chemicals, using metered spray technology, into the immediate vicinity of the operator. The disclosed mechanism is particularly oriented toward use by an individual sitting at a desk using a microcomputer. Similarly, U.S. Pat. No. 5,724,256 to Lee et al. discloses a computer controlled odor mixing and dispensing system suitable for use in conjunction with a multimedia computer application. Neither of these systems are designed for, or suitable for, providing an aroma to a larger area such as one or more rooms of a home or office. Furthermore, they are not adapted for delivering an aroma from scented oil.

U.S. Pat. No. 4,603,030 to McCarthy, U.S. Pat. No. 5,832,320 to Wittek, and U.S. Pat. No. 5,972,290 to De Sousa each describe scent-emitting systems designed to provide a variety of scents to intensify sensorial perception of an audience in attendance of a visual and/or acoustical representation, by introducing scents in synchronism with the visual and/or acoustic representation. However, the aforementioned systems are complex, expensive and adapted for emitting scents over a very large area such as a movie theater.

Accordingly, there is an existing need for a scent emitting system particularly suited for use in a home, workplace, or like environment that overcomes the aforementioned disadvantages and limitations of the aforementioned prior art systems.

SUMMARY OF THE INVENTION

The present invention provides an electric/electronic scent-emitting system configured for selectively delivering predetermined scents generated by scented oils contained within scent cartridges to a proximate surrounding environment.

In one aspect of the present invention, an electronic, mechanically actuated, multi-cartridge scent-delivery system is provided. A system housing defines a tray-receiving opening extending into an interior space and configured for supporting a tray within the interior space and movable between open and closed positions. A plurality of cartridges each containing selected scented fluids are seated within tray pockets. A corresponding plurality of independent mechanically actuated rocker arms are provided, each having an end configured for actuating a particular one of the cartridges into an open position to release a respective scent. A blowing means is provided for creating and subsequently directing a flow of air over the scent cartridges for egress through housing vents. Preferably, heating means are provided for heating the scented fluids contained within the cartridges to increase the strength of the emitted scents. Furthermore, a fan-speed control mechanism is preferably provided for varying the scent coverage area, and a timer is preferably provided for controlling the duration of scent emission and/or pre-setting a time of operation.

In another aspect of the present invention, an electronic, electro-mechanically actuated, single-cartridge scent-delivery system is provided. A system housing defines a tray-receiving opening and an interior space. A tray is provided supported by interior housing guide rails and manually slidable through the tray-receiving opening between opened and closed positions by means of a pressure release locking mechanism. A cartridge containing a scented fluid is provided seated within a tray pocket. An electromechanical actuation member positioned over the cartridge selectively actuates the cartridge between a closed position and an open position by vertical displacement of the actuating member. A blowing means is provided for creating and subsequently directing a flow of air over the scent cartridge for egress through housing vents. Preferably, heating means are provided for heating the scented fluid contained within the cartridge to increase the strength of the emitted scent. Furthermore, a fan-speed control mechanism is preferably provided for varying the scent coverage area, and a timer is preferably provided for controlling the duration of scent emission and/or pre-setting a time of operation.

In a further aspect of the present invention, an electric, manually actuated, single-cartridge scent-delivery system is provided. The system is contained within a housing structure defined by a main housing body and a housing lid cooperating therewith to define an interior space. A scent-emitting cartridge is supported within an interior housing pocket and a blowing means is provided for creating and subsequently directing a flow of air over the scent cartridge for egress through housing vents. An actuating structure depends downwardly from an interior surface of the housing lid such that the structure actuates the cartridge toward an open position as the housing lid is closed against the main housing body. Preferably, a switch controlled heating means is provided for heating the scented fluid contained within the cartridge to increase the strength of the emitted scent.

In yet another aspect of the present invention, an electric, manually driven, mechanically actuated scent-delivery system is provided having the form and appearance of an electric candle. The system includes pivotally cooperating upper and lower housing bodies defining an interior space. An interior support structure is supported within the lower housing body and includes an integral pocket for supporting a scent-emitting cartridge. A fan is provided attached to the support structure for drawing air into the interior space and communicating the air over the scent-emitting cartridge and through vent openings in the housing. A fan speed control switch is provided for enabling user control over the coverage area of the scent during operation. A heating means is provided for heating scented fluid contained within the cartridge, thereby increasing the strength of the emitted scent. A manually manipulated mechanical actuation subassembly is provided for selectively actuating the cartridge between opened and closed positions, as well as selectively actuating an internal power supply switch. The mechanical actuation subassembly includes an actuation member having a contact portion extending through an aperture in the housing top. The contact portion is particularly configured to have the form and appearance of a candle wick. Furthermore, an internal light source, such as a light-emitting diode (LED), is preferably positioned near a base of the contact portion to enable transmission of light therethrough. In this manner the contact portion mimics the appearance of a lighted candle wick.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF THE PREFERRED EMBODIMENTS

Shown throughout the figures, the present invention is generally directed to an electric/electronic portable scent delivery system for use in homes, offices and the like. Various embodiments of the system are described below. However, the systems each include a scent-delivery unit configured for actuating specially configured scent cartridges either by mechanical actuating means, including electro-mechanical and manually-driven mechanical means, or by manual actuating means. Significantly, the system design facilitates the installation and/or removal of the scent cartridges, enabling an end user to efficiently and conveniently select a desired scent or aroma. In addition to facilitating scent selection, the various embodiments of the system incorporates means for enabling end user control over the strength of the emitted scent, the coverage area of the emitted scent, and the duration of scent emission.

The Scent Cartridge

The various embodiments of the present invention are each adapted for use with a scent-emitting cartridge having a unique construction. The cartridge structure has been previously described in co-pending application Ser. No. 09/902,307, filed by the same inventor on Jul. 10, 2001, and incorporated herein by reference. However, the following description of the cartridge is provided in an effort to facilitate an understanding of the cartridge as incorporated into the particular system embodiments described herein.

Figure 1:
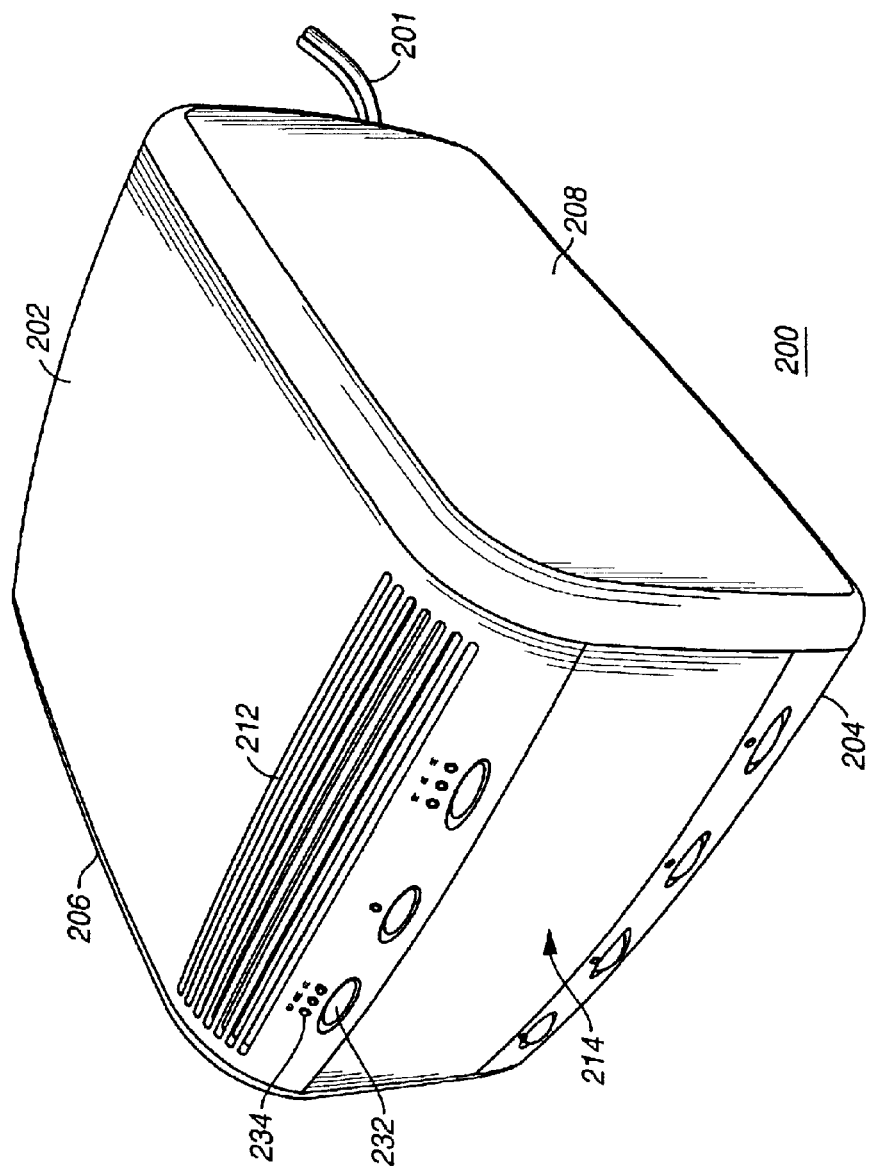
FIG. 1 is a perspective view of an electronic, mechanically actuated, multi-cartridge scent-delivery system in accordance with a preferred embodiment of the present invention, wherein the scent cartridge supporting tray is depicted in a closed position.
Figure 2:
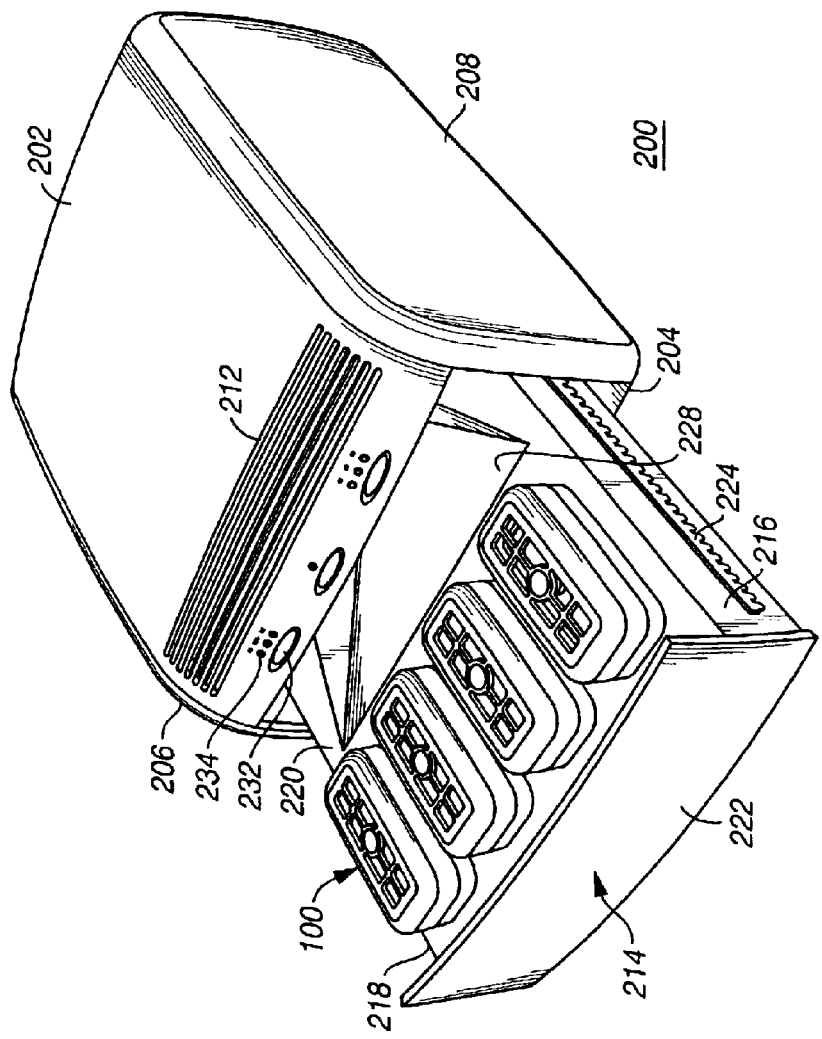
FIG. 2 is a perspective view of the multi-cartridge scent delivery system of FIG. 1, wherein the scent cartridge supporting tray is depicted in a fully opened position.
Figure 3:
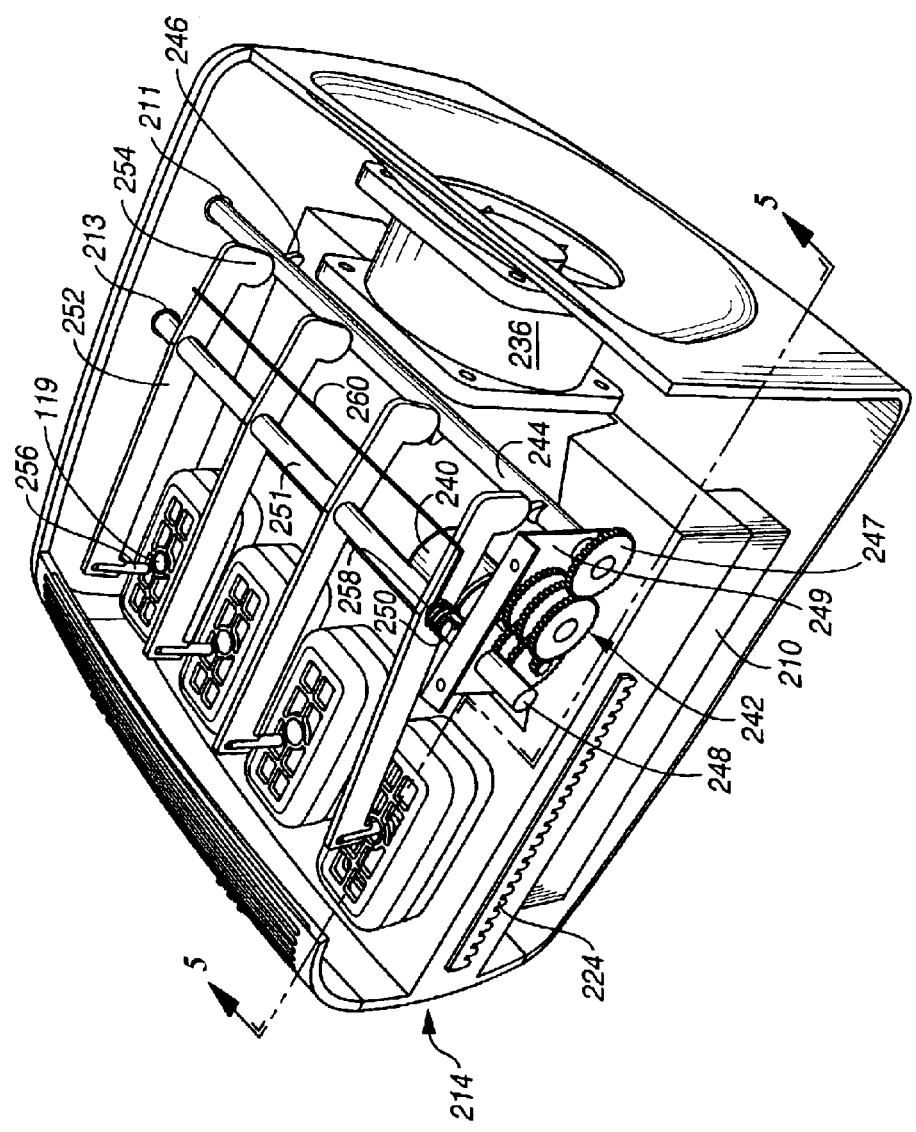
FIG. 3 is a perspective view of the multi-cartridge scent delivery system of FIG. 1 with the top and right sides of the housing removed to expose the interior of the system.
Figure 4:
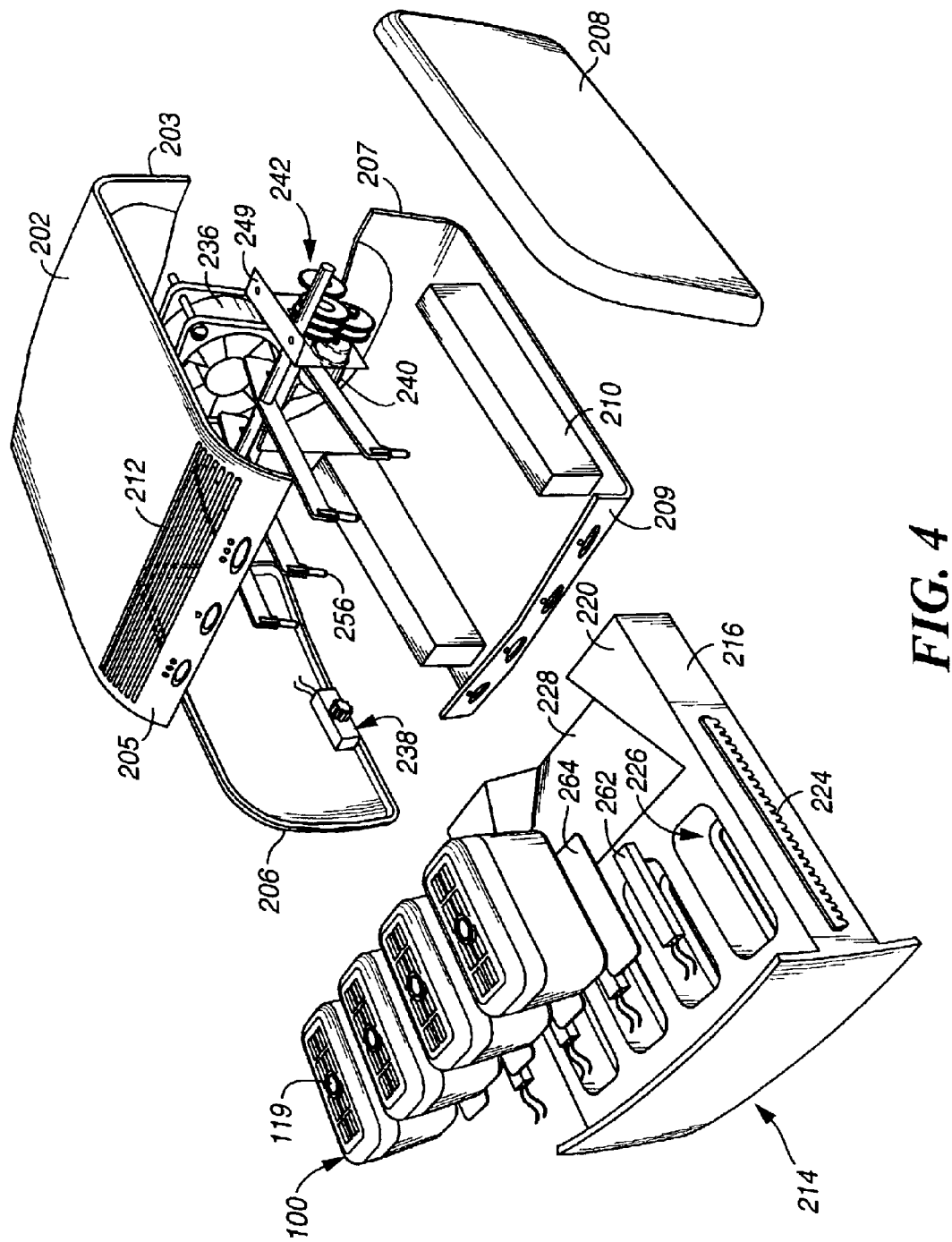
FIG. 4 is an exploded perspective view of the multi-cartridge scent delivery system of FIG. 1.
Figure 5:
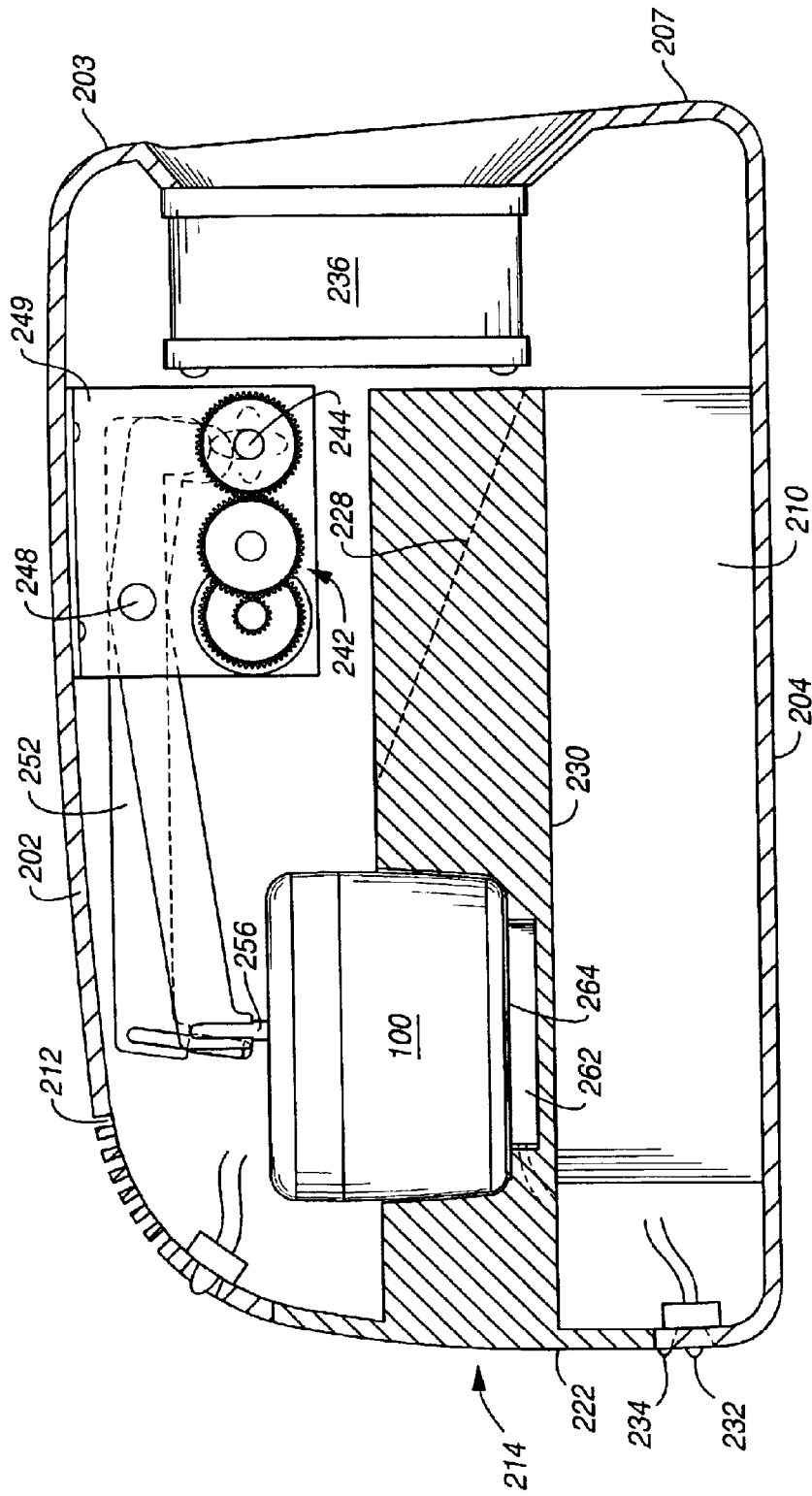
FIG. 5 is a full section view taken along cut line 5—5 of FIG. 3, with only the housing and tray shown in section.
Figure 6:
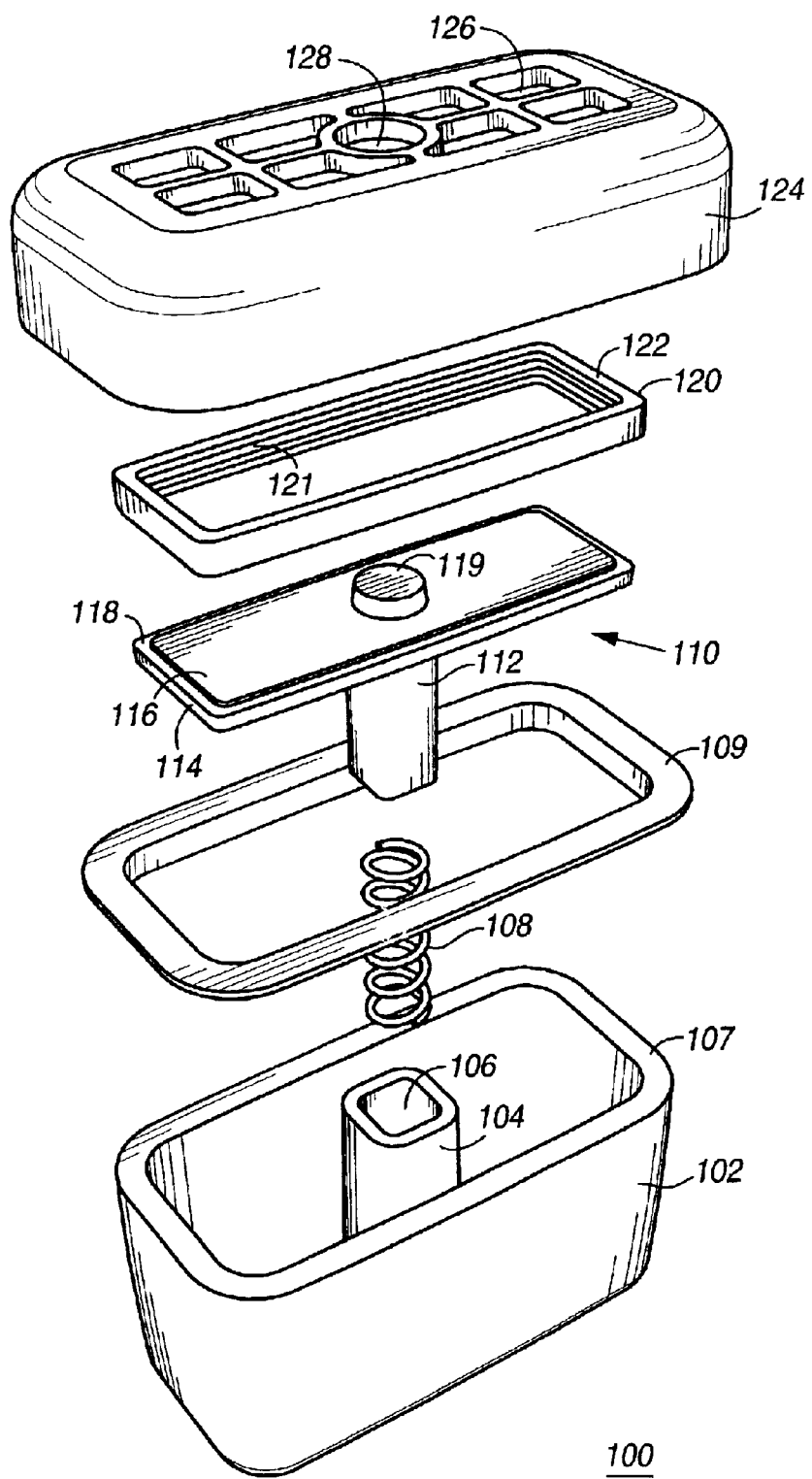
FIG. 6 is an exploded perspective view of a scent-containing cartridge in accordance with the present invention.
Figure 8:
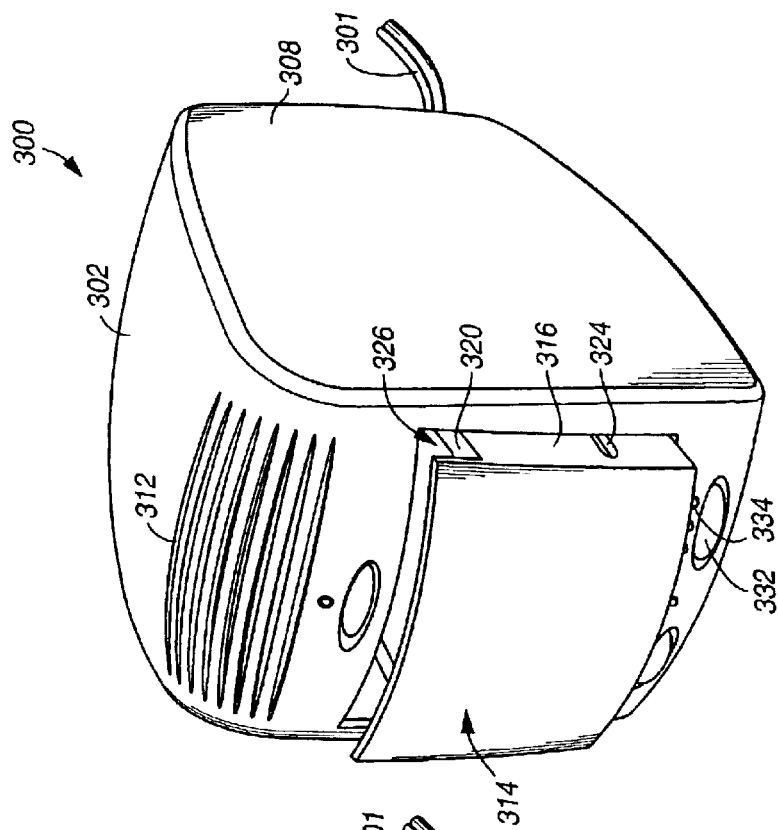
FIG. 8 is a perspective view of the scent delivery system of FIG. 7, wherein the scent cartridge supporting shelf is shown in a slightly opened position.
Figure 7:
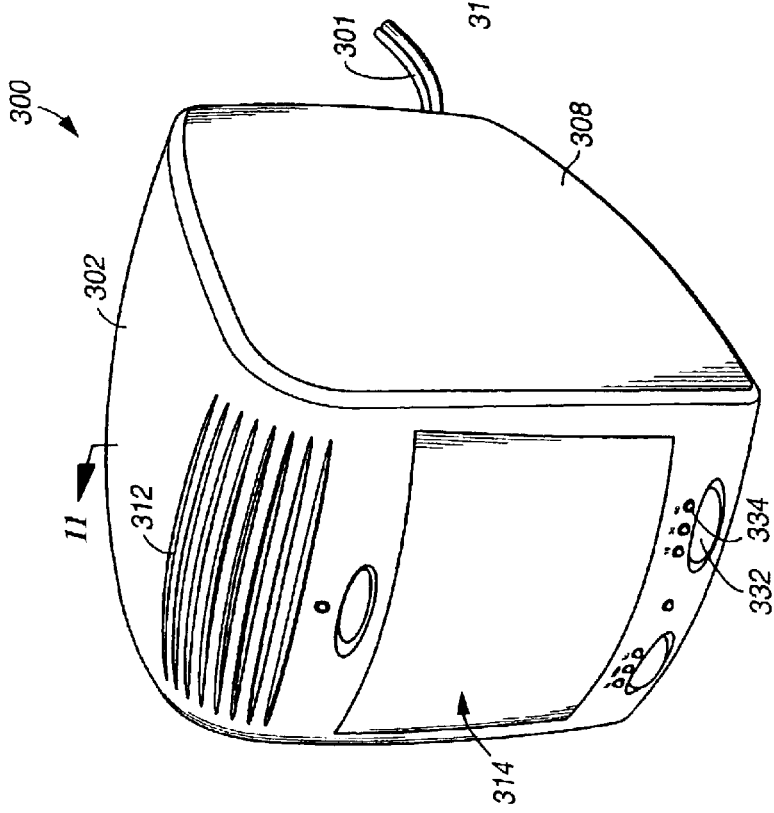
FIG. 7 is a perspective view of an electronic, electro-mechanically actuated, single-cartridge scent-delivery system in accordance with a further embodiment of the present invention, wherein the scent cartridge-supporting tray is shown in a closed position.
Figures 9, 10:
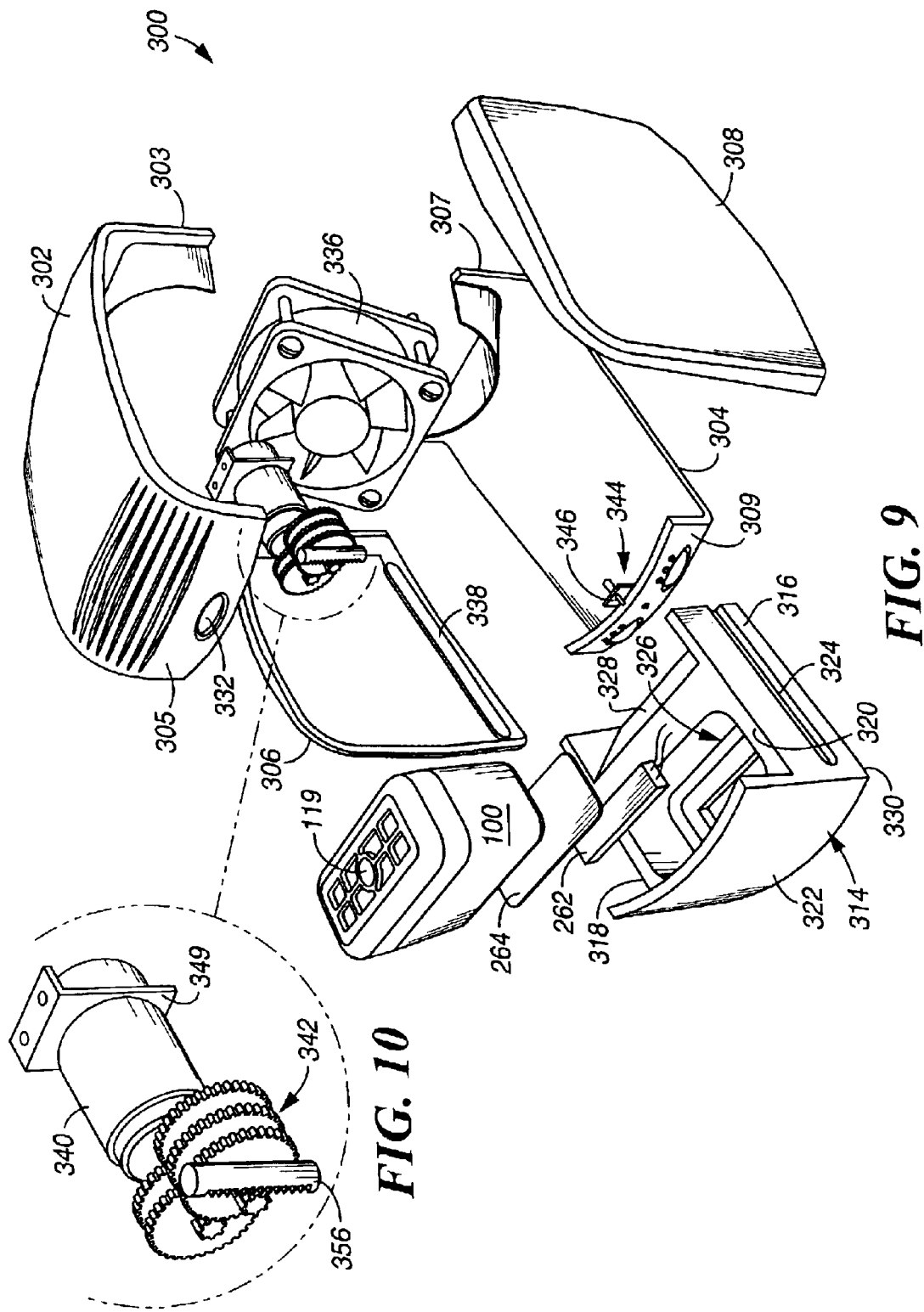
FIG. 9 is an exploded perspective view of the scent delivery system of FIG. 7.
FIG. 10 is a magnified and isolated perspective view of the cartridge actuating mechanism depicted in FIG. 9.

Referring briefly to FIG. 6, scent cartridge assembly 100 includes a lower housing body 102 and an upper housing cap 124 separated by a sealing gasket member 109 interposed between respective abutting edges 107 and 123. The lower housing body 102 and upper housing cap 124 are preferably molded from a polymer having a melting temperature ($T_m$) sufficiently high to prevent melting of the housing from cartridge heating during system operation. The housing can be constructed from either transparent or opaque polymers. In some instances, a transparent housing may be preferred to enable a system operator to periodically inspect a cartridge scent oil level to determine whether cartridge replacement is necessary.

Lower housing body 102 includes an integral upwardly extending walled body 104 defining a channel 106. A T-shaped member, shown generally as reference numeral 110, includes a base 114 having an integral body 112 depending downwardly therefrom. The outer surface of body 112 is sized and shaped for enabling body 112 to be snugly received within channel 106. Compression spring 108, or an alternate compression member, is received within channel 106 of walled body 104. Preferably, the upper end of compression spring 108 does not extend beyond the upper end of body 104 in its non-compressed equilibrium state. T-member body 112 is received within channel 106 such that it remains supported by the upper end of compression member 108. In this manner, when body 112 is received within channel 106, the spring 108 acts to bias T-shaped member 110 in an upward direction.

Base 114 of T-member 110 is provided having a raised upper surface portion 116 defining a peripheral ledge 118. Furthermore, raised surface portion 116 has a centrally positioned nub 119 protruding upwardly therefrom. Nub 119 is sized, shaped and oriented to extend through aperture 128 in housing cover 124 when the cartridge is fully assembled. Gasket member 120 is provided having a continuous interior peripheral groove 121 sized and shaped for being sealingly fitted about ledge 118 of T-shaped member 110.

In addition to nub receiving aperture 128, upper housing cap 124 includes a plurality of apertures 126 for enabling the passage or communication of scents from the cartridge interior.

Lower housing body 102 is filled with a volume of scented oil (not shown), preferably to a level at least slightly below the upper end 107 of lower housing body 102. When the cartridge is fully assembled, the cartridge compression spring 108 biases T-shaped member 110 upwardly such that gasket 120 forms a substantially air tight seal against the inner surface of housing cap 124. In this manner, the gasket prevents the emission of any scent or aroma emanating from the scented oil in housing base 102 through the housing cover apertures 126, 128. Cartridge 100 can be actuated into an open position by providing a downward force against nub 119. In particular, downward actuation of nub 119 causes corresponding downward displacement of T-member 110, thereby breaking the seal formed around the cartridge apertures 126, 128 to enable the emission of scented fumes therethrough.

Throughout the specification, reference is made to the actuation of the scent cartridge into an open position by the force of an actuating structure or member against nub 119. As previously described, nub 119 is an integral structure formed upon the upper surface of T-member 110. As will be apparent to those skilled in the art, nub 119 is merely provided as a convenient contact point for applying a downward force against T-member 110. Consequently, T-member 110 could just as easily be formed without nub 119. In that case, the force of a particular actuating structure could be applied directly to the upper surface of T-member 110. Accordingly, any reference herein to the actuation of nub 119, making contact with nub 119, etc. are not intended to be limiting. That is, actuating nub 119 is intended to be equivalent to actuating T-member 119.

First Scent System Embodiment

Referring now to FIGS. 1–5, an electronic, mechanically actuated, multi-cartridge scent delivery system, shown generally as reference numeral 200, is illustrated in accordance with a first embodiment of the present invention. The main components of the system are contained within a housing structure generally defined by top 202, bottom 204, left side 206, right side 208, and front face 222 of tray 214. Housing top 202 is provided having integral vent openings 212 through which scents are emitted from the interior of the housing to a proximate external environment. As further described below, function buttons 232 are provided extending through curved front portion 205 of housing top 202 and curved front portion 209 of housing bottom 204 for controlling the operation of the system. Visual display means, such as Light-Emitting Diodes (LEDs) 234 are preferably provided for communicating current settings during operation.

System tray 214 is supported at its bottom surface 230 by interior housing supporting feet 210. Motorized pinions 238 mounted to the interior housing surface cooperate with racks 224 running along the sides 216, 218 of the tray 214 to effect forward and rearward tray movement. In this manner, the tray can be automatically opened and closed via one of the external control buttons 232 electrically coupled to the pinion mechanism. Pockets 226 formed in upper surface 220 are sized and shaped for snugly receiving cartridges 100 therein. Preferably, each pocket 226 includes an electrically controlled heating member 262 supported at its bottom, and a heat diffusion member 264 interposed between the bottom surface of the cartridge 100 and the top side of heating member 262. The heating member 262 is provided for imparting heat to the scented fluid within cartridge 100, thereby increasing the strength of the emitted aroma. The top surface 220 of tray 214 includes a sloped or tapered area 228 for directing a flow of air generated by fan 236 over the top sides of the cartridges and toward vent openings 212. Fan 236 is preferably mounted between rear downward curved portion 203 of housing top 202 and rear upward curved portion 207 of housing bottom 204. Preferably, the fan speed is variable to enable user control over the scent coverage area.

A first horizontally disposed shaft 248 has a left end received within left housing side wall depression 213 and a right end supported through an opening in bracket member 249, itself secured to the interior surface of housing top 202. Shaft 248 is secured in a manner preventing its rotation. As will be apparent to those skilled in the art, myriad means for preventing such rotation are possible. For example, the left end of shaft 248 can be permanently fixed within depression 213 using a high strength epoxy adhesive. Alternatively, the left end of shaft 248 can be temporarily fixed against rotation, for example, by providing a threaded shaft end and a corresponding threaded receiving depression.

A second horizontally disposed shaft 244 has a left end captivated within left housing side wall depression 211 and a right end supported through an opening in bracket 249 such that shaft 244 can rotate freely about its central axis. A plurality of cams 246 are provided in a spaced-apart relation along shaft 244, each positioned for engagement with an end portion 254 of a corresponding rocker arm 252. Furthermore, the cams 246 are provided radially offset from one another about shaft 244.

A plurality of rocker arms 252 are provided pivotally mounted about shaft 248 and separated by hollow cylindrical spacers 251 to prevent longitudinal movement, or sliding, along shaft 248. Each rocker arm 252 has a cartridge-actuating portion 256 depending downwardly from its forward end and positioned for contacting a respective cartridge nub 119 when pivoted downward. Furthermore, each rocker arm 252 has a cam-engaging portion 254 depending downwardly from its rearward end.

A torsion spring 258 is provided mounted about shaft 248. A first end of the torsion spring is secured within shaft aperture 250. A straight length 260 of torsion spring 258 extends over and against the rocker arms to pivotally bias the cartridge-actuating portions 256 of the rocker arms away from the respective cartridge nubs 119, and the rear end portions 254 of the rocker arms against shaft 244.

A gear assembly 242 driven by motor 240 is provided for effecting rotation of shaft 244. During such rotation, engagement of a particular cam 246 against the end 254 of a particular rocker arm 252 forces the rocker arm to pivot about shaft 248 and thereby cause rocker arm cartridge-actuating portion 256 to force corresponding cartridge nub 119 downward. In this manner, selective actuation of the cartridges 100 into an open position can be achieved by merely controlling the degree of rotation of shaft 244.

Preferably, each scent-containing cartridge is associated with an individual control button on the front of the system housing such that a user can effect the emission of a desired scent by merely pressing the associated control button. In operation, upon pressing the button associated with the user-selected scent, shaft 244 rotates until the appropriate cam 246 engages the respective rocker arm end 254 to effect actuation of the corresponding cartridge nub 119 of the cartridge 100 containing the desired scent.

Additional control buttons are provided for controlling other system functions including, for example, system power, fan speed, and cartridge heating temperature, to name just a few. Additionally, a timer can be provided for selecting the duration of emission of a particular scent and/or to pre-select a time of operation. Electrical power is provided to the system via power input means 201.

Second Scent System Embodiment

Referring now to FIGS. 7–11, an electronic, electromechanically actuated, single-cartridge scent delivery system, shown generally as reference numeral 300, is illustrated in accordance with a second embodiment of the present invention.

The main components of the system are contained within a housing structure generally defined by top 302, bottom 304, left side 306, right side 308, and front face 322 of tray 314. Housing top 302 is provided having integral vent openings 312. Control buttons 332 are provided extending through curved front portion 305 of housing top 302 and curved front portion 309 of housing bottom 304 for controlling the operation of the system. Visual display means, such as Light-Emitting Diodes (LEDs) 334 are preferably provided for communicating current settings during operation.

System tray 314 is slidably supported by interior housing wall guide rails 338 cooperating with grooves 334 extending along tray sides 316 and 318. A pocket 326 formed in upper surface 320 is sized and shaped for snugly receiving cartridge 100 therein. Preferably, pocket 326 includes an electrically controlled heating member 262 and heat diffusion member 264 in a manner similar to that previously described with respect to the multi-cartridge system embodiment. The top surface 320 of tray 314 includes a sloped or tapered area 328 for directing a flow of air generated by fan 336 over the top side of the cartridge 100 and toward vent openings 312.

Figure 11:
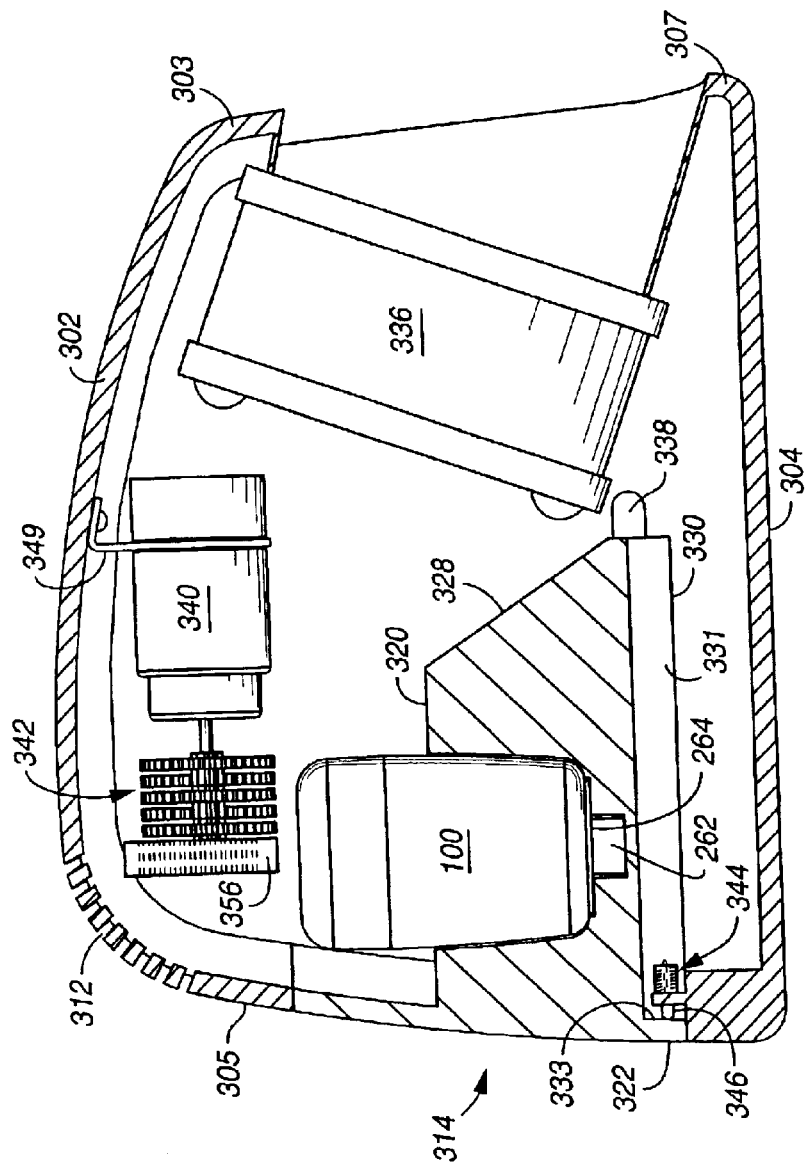
FIG. 11 is a full section view through the housing and cartridge supporting shelf taken along cut line 11—11 in FIG. 7.

A pressure release mechanism 344 is provided attached to the interior surface of curved housing portion 309 for manually controlling the opening and closing of tray 314. The tray bottom 330 is provided having a channel 331 for enabling interference-free sliding of the tray over the pressure release mechanism 344. As best depicted in FIG. 11, interior surface 333 of tray front face 322 engages an actuating pin 346 extending outwardly from pressure release mechanism 344. Such pressure release mechanisms are well known in the art and further description is not provided. When the tray is in a closed position, front face 322 is substantially flush with the outer surfaces of housing portions 305 and 309. The tray can be opened from a closed position by applying light pressure to front face 322. In this manner, pin 346 is actuated outward against surface 333 causing the tray to open slightly and creating enough of a space for the user to grasp the upper edge of the tray for further opening.

A motor 340 is provided secured to the interior surface of housing top 302 by a bracket 349. Motor 340 drives gear mechanism 342 that, in turn, engages vertically disposed actuating member 356 for upward and downward movement. Actuating member 356 is positioned directly above cartridge nub 119 when tray 314 is in a closed position. Consequently, during downward movement member 356 engages T-member 110 to effect actuation of cartridge 100 into an open, scent-emitting position. Function buttons enable user control of system power, cartridge heating, fan operation, and cartridge actuation.

As will be apparent to those skilled in the art, myriad alternative electromechanical means could be employed for imparting a downward force against T-member 110 to effect actuation of cartridge 100 into an open position without departing from the intended scope of the invention. For example, a solenoid could be positioned directly over T-member 110. Alternatively, a motor/gear box could be provided rotating a cam driving a vertically actuated member downward against T-member 110. Furthermore, a worm gear could be used to drive a cooperating actuating member downward against T-member 110.

Third Scent System Embodiment

Figure 13:
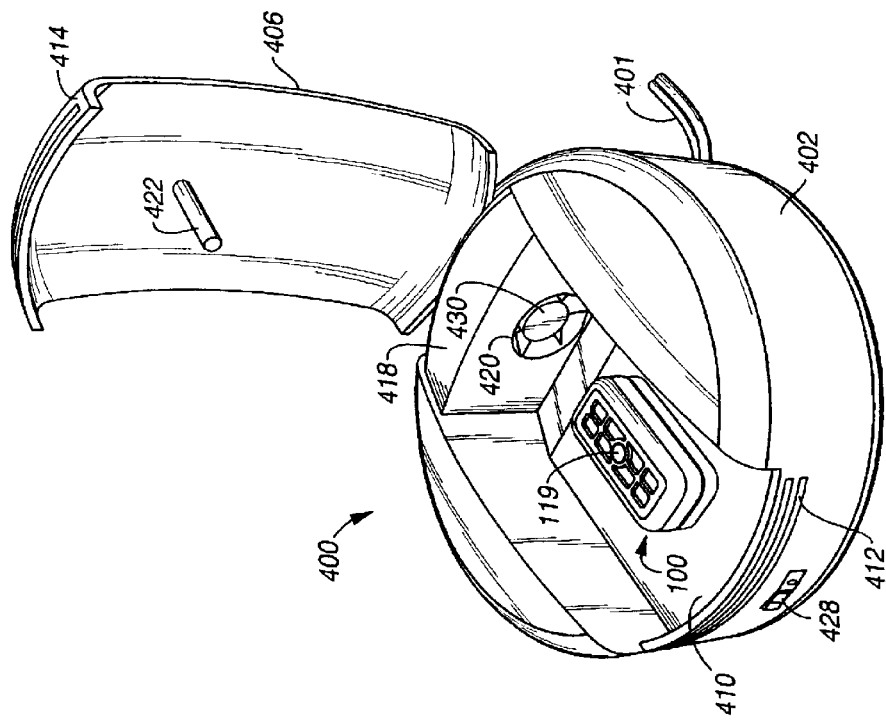
FIG. 13 is a perspective view of the single-cartridge scent delivery system of FIG. 12, with the housing lid opened to show the system interior.
Figure 12:
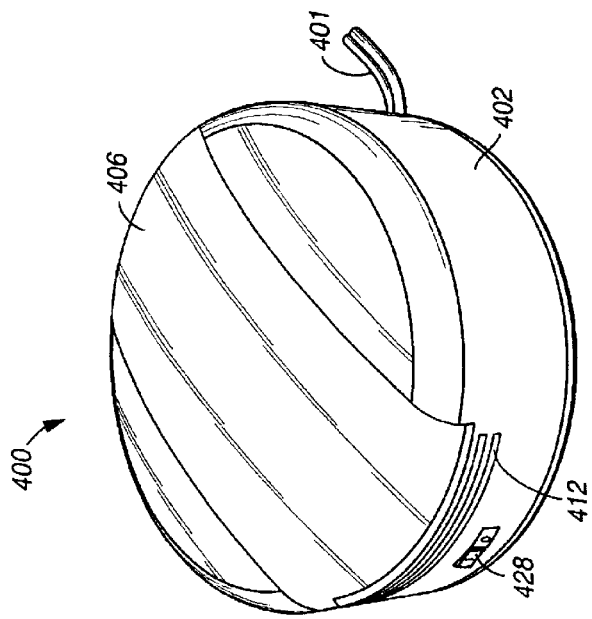
FIG. 12 is a perspective view of an electric, manually actuated, single-cartridge scent-delivery system in accordance with a further embodiment of the present invention, wherein the housing lid is depicted in a fully closed position.
Figure 14:
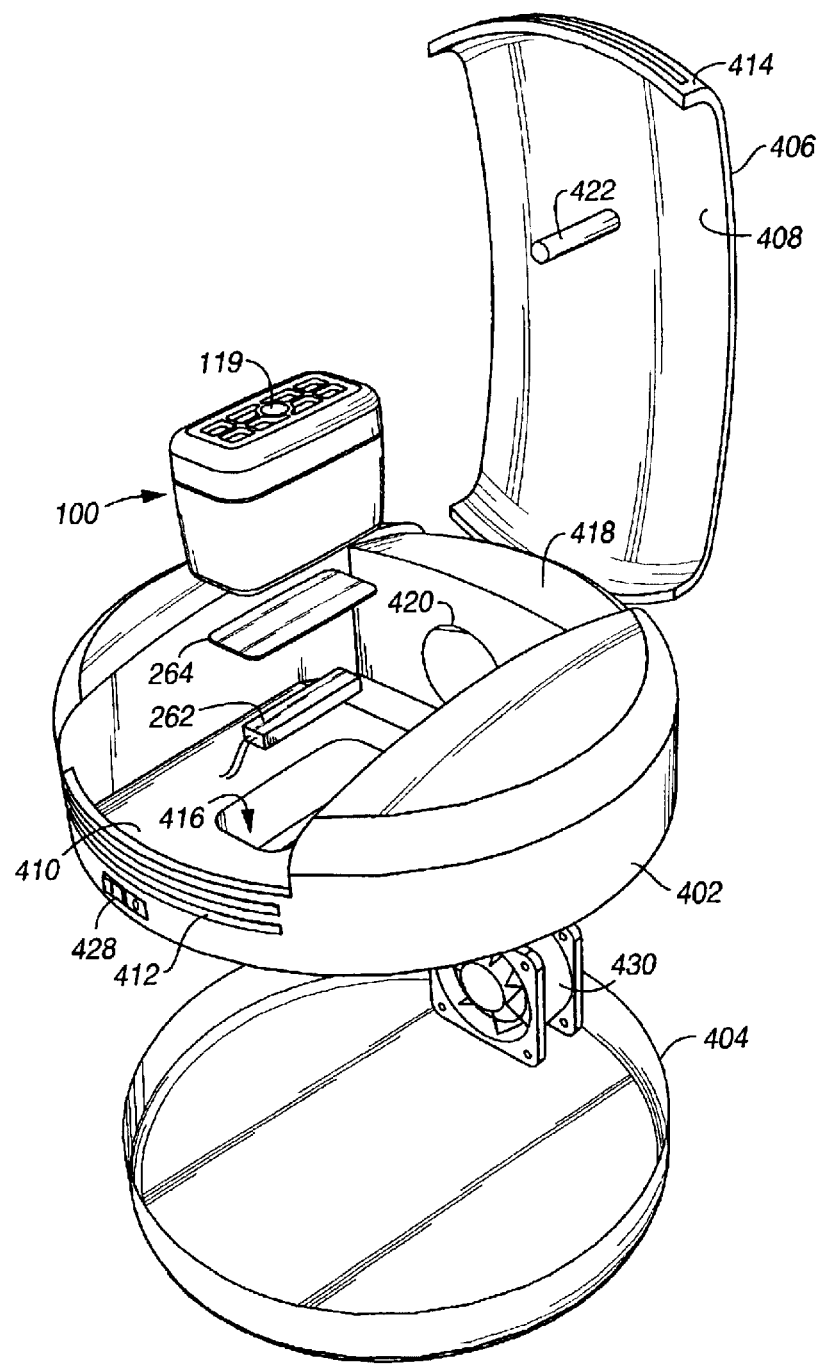
FIG. 14 is an exploded perspective view of the single-cartridge scent delivery system of FIG. 12.
Figure 15:
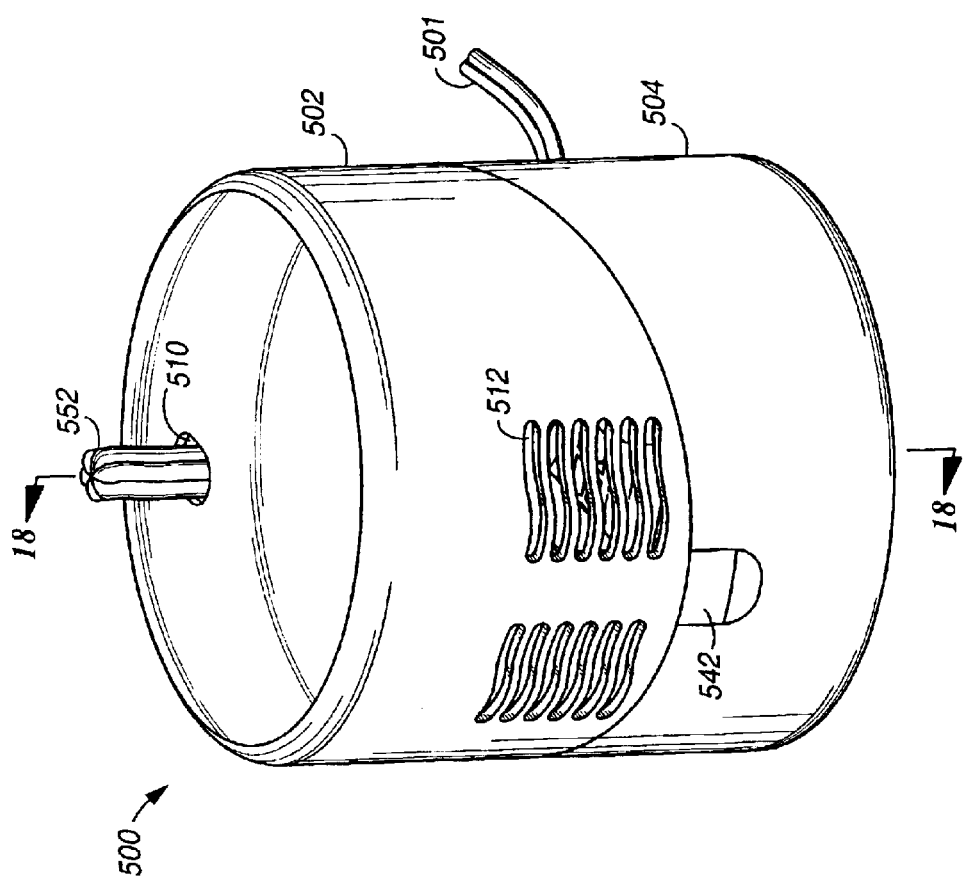
FIG. 15 is a perspective view an electric, manually driven, mechanically actuated single cartridge scent-delivery system with the housing top illustrated in a closed position, in accordance with a further embodiment of the present invention.
Figure 16:
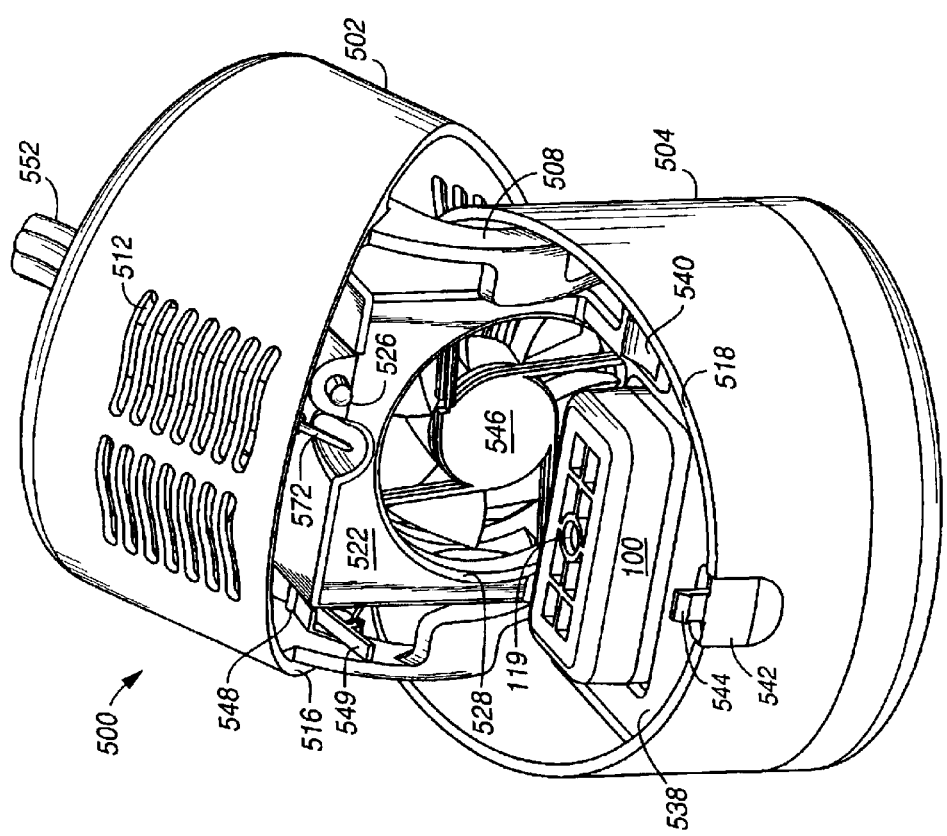
FIG. 16 is a perspective view of the scent delivery system of FIG. 15 with the housing top illustrated in an opened position to expose the system interior.
Figure 17:
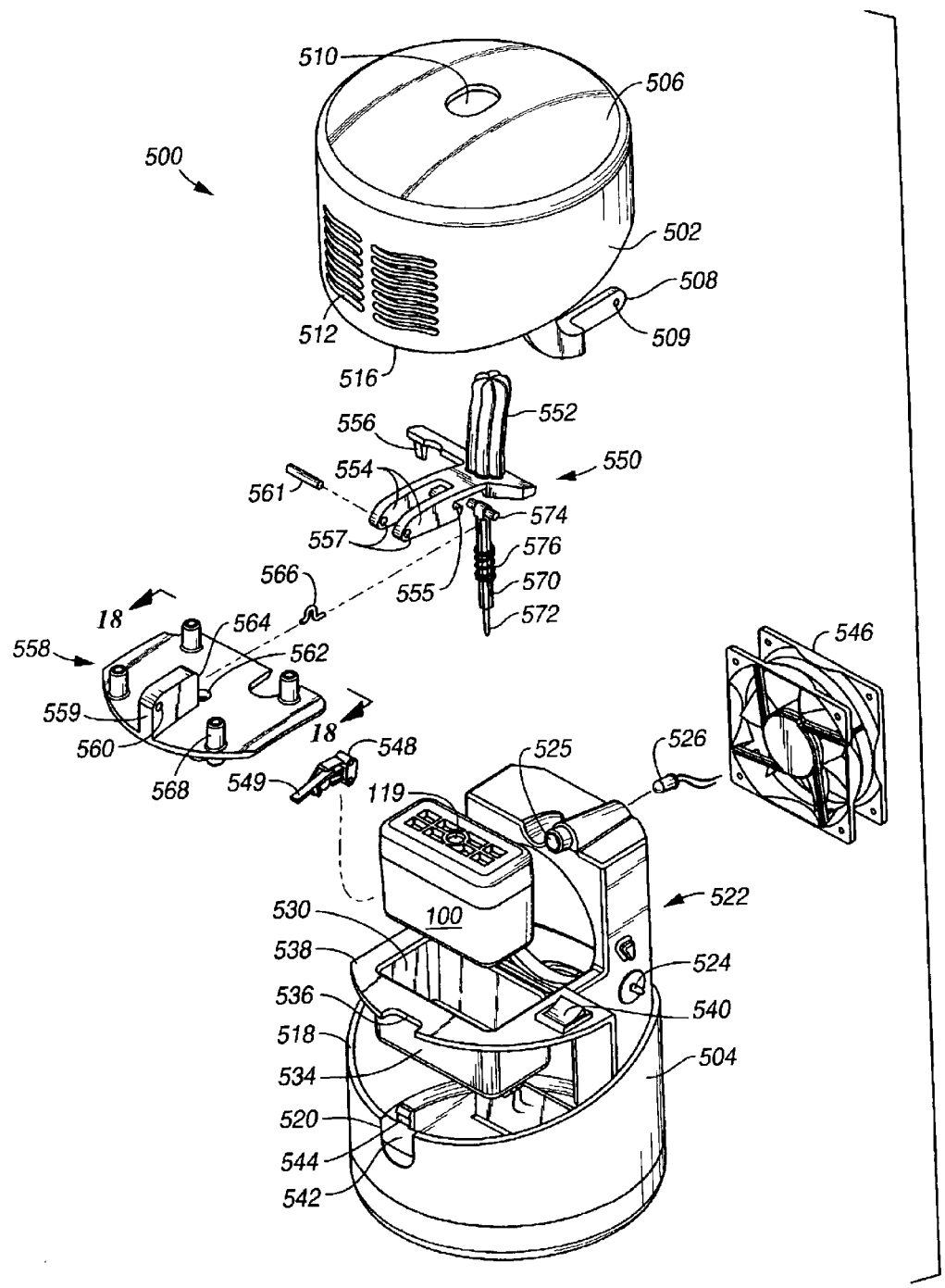
FIG. 17 is an exploded perspective view of the scent delivery system of FIG. 15.
Figure 18:
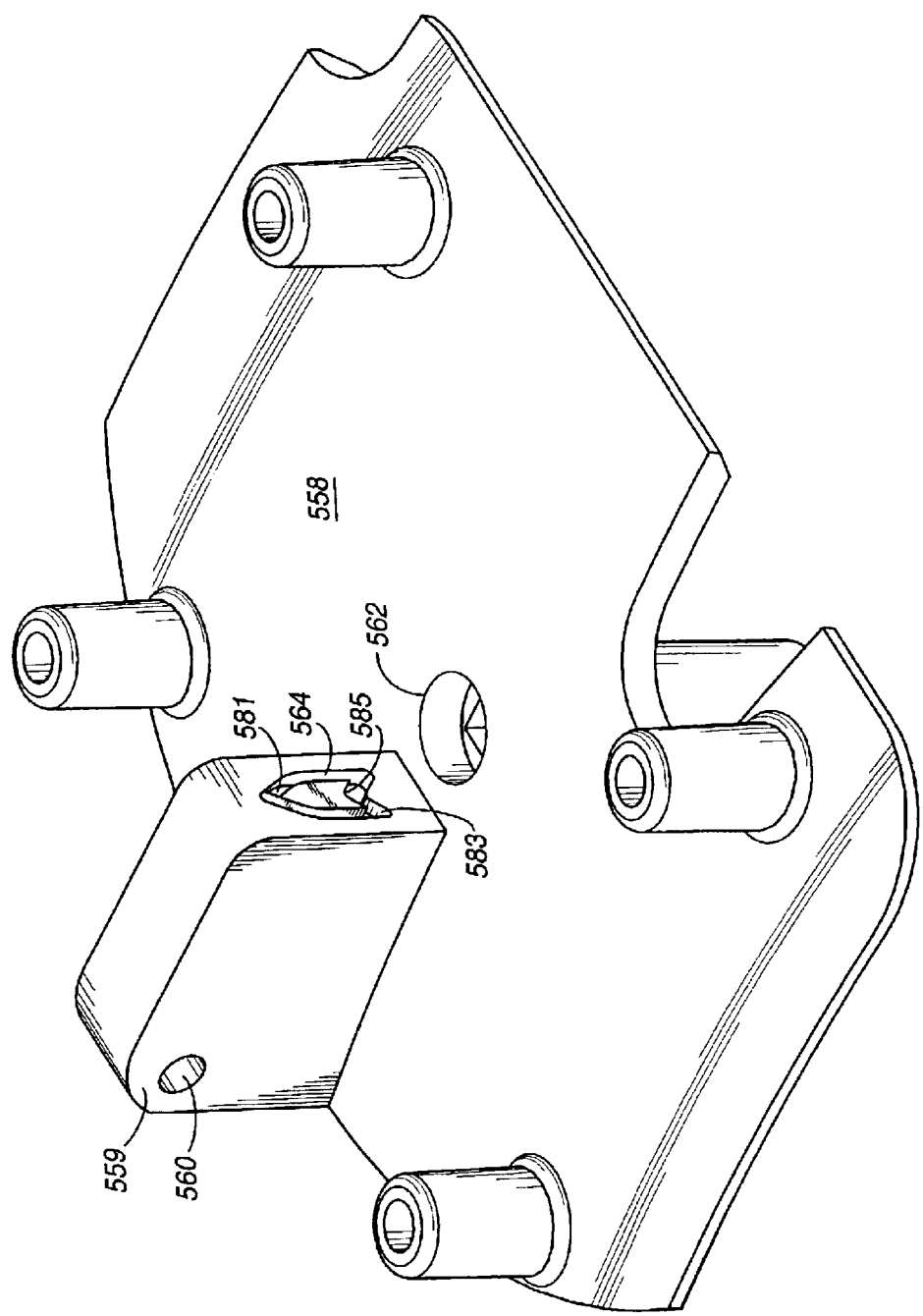
FIG. 18 is a magnified perspective view of the baffle 558 of FIG. 17.

Referring now to FIGS. 12–14, an electric, manually actuated, single-cartridge scent delivery system, shown generally as reference numeral 400, is illustrated in accordance with a third embodiment of the present invention.

The main components of the system are contained within a housing structure generally defined by main body 402, base 404 and cover 406. Main body 402 is provided having integral vent openings 412 extending therethrough. A main horizontal surface is provided having a cartridge-retaining pocket 416 formed therein. Preferably, a heating member 262 and heat diffusion member 264 are provided within pocket 416 in the same manner as previously described for controlling the strength of an emitted aroma. A fan 420 is provided attached to a rear vertical wall portion 418 of main body 402 and positioned for directing a flow of air through an opening 420 formed therein. Preferably, means are provided for varying fan speed, thereby enabling user control over the scent coverage area.

A multi-position switch 428 is provided for controlling operation of the fan 420 and heating member 262. Cover 406 has an integral cartridge-actuating member 422 depending downwardly from an interior surface 408 and positioned such that member 422 engages nub 119 of cartridge 100 when cover 406 is in a closed position. In this manner, T-member 110 is downwardly displaced such that cartridge 100 is actuated into an open, scent-emitting orientation.

As will be apparent to those skilled in the art, myriad alternative manual actuation means could be employed for imparting a downward force against T-member 110 to effect actuation of cartridge 100 into an open position without departing from the intended scope of the invention. For example, a threaded lid having a downward depending interior surface structure positioned over T-member 110 could be employed, wherein downward motion of the structure during twist-on lid attachment effects the desired cartridge actuation. Alternatively, an independent structure supported within the housing interior could be positioned such that it is contacted by an interior lid surface during lid attachment, thereby driving the independent support structure against the cartridge to achieve actuation thereof into an open position for scent emission.

Fourth Scent System Embodiment

Referring now to FIGS. 15–19, an electric, manually-driven, mechanically-actuated, single-cartridge scent delivery system, shown generally as reference numeral 500, is illustrated in accordance with a fourth embodiment of the present invention.

The main structural components of the system include housing upper body 502, housing lower body 504, interior structural support body 522, baffle member 558, and actuation member 550. The details of the aforementioned structural components, as well as their cooperation with one another and interaction with other system components, will now be described in greater detail.

Housing upper body 502 is provided pivotally attached to support body 522 by arms 508. More particularly, the arms 508 are provided fixed at their upper ends (not shown) to the interior surface of housing upper body 202 and pivotally secured at their lower ends to outwardly extending support body pins 524 received through lower arm apertures 509. When upper housing body 502 is pivoted forward toward a closed orientation, lower peripheral edge 516 abuts upper peripheral edge 518 of lower housing body 504. For aesthetic purposes, the upper and lower housing bodies are preferably shaped to resemble a candle when the upper housing body 502 is in a closed position. As will be apparent to those skilled in the art, various alternative pivotal connection arrangements could be employed without departing from the intended scope of the invention.

A generally U-shaped latch member 542 is provided pivotally attached to the front interior surface of lower housing body 504 about support pegs 513 extending outwardly from lower housing body tabs 511. Latch member 542 is sized and shaped to extend through a corresponding U-shaped slot 520 provided in lower housing body 504. Preferably, latch 542 is forwardly biased in a counterclockwise orientation about pivot point 513 using a torsion spring (not shown) or other such biasing mechanism, as is well known to those skilled in the mechanical arts. Latch 542 has an integral catch 544 sized and shaped for engaging an upper housing interior surface recess 545. In this manner, as the upper housing body 502 is pivoted downward toward lower housing body 504, the catch 544 engages recess 545 providing the desired latching. Correspondingly, upon pressing the latch 542, catch 544 becomes disengaged from recess 545 to enable opening of upper housing 502. As will be apparent to those skilled in the art, myriad other latching means could be employed for selectively latching the upper and lower housing bodies to each other without departing from the intended scope of the invention.

Support body 522 preferably has a unitary molded construction configured to fit snugly within lower housing body 504. As previously described, support body 522 is utilized to provide pivotal support of upper housing body 502. As will now be described, support body 522 also includes a variety of structural features for supporting the internal structural elements and components of the system.

Support body upper surface 538 includes a downwardly extending pocket 530 defined by pocket walls 534. Preferably, pocket 530 is sized and shaped such that scent cartridge 100 can be snugly seated therein. The lower surface of scent cartridge 100 rests upon a heat diffusion member 264 supported by a bottom wall of pocket 530. An electric heating member 262 extends through an opening in the bottom wall of pocket 530 and contacts the lower surface of heat diffusion member 264. As will be apparent to those skilled in the art, myriad other means for heating the scented oil in cartridge 100 could be employed without departing from the intended scope of the invention.

Figure 19:
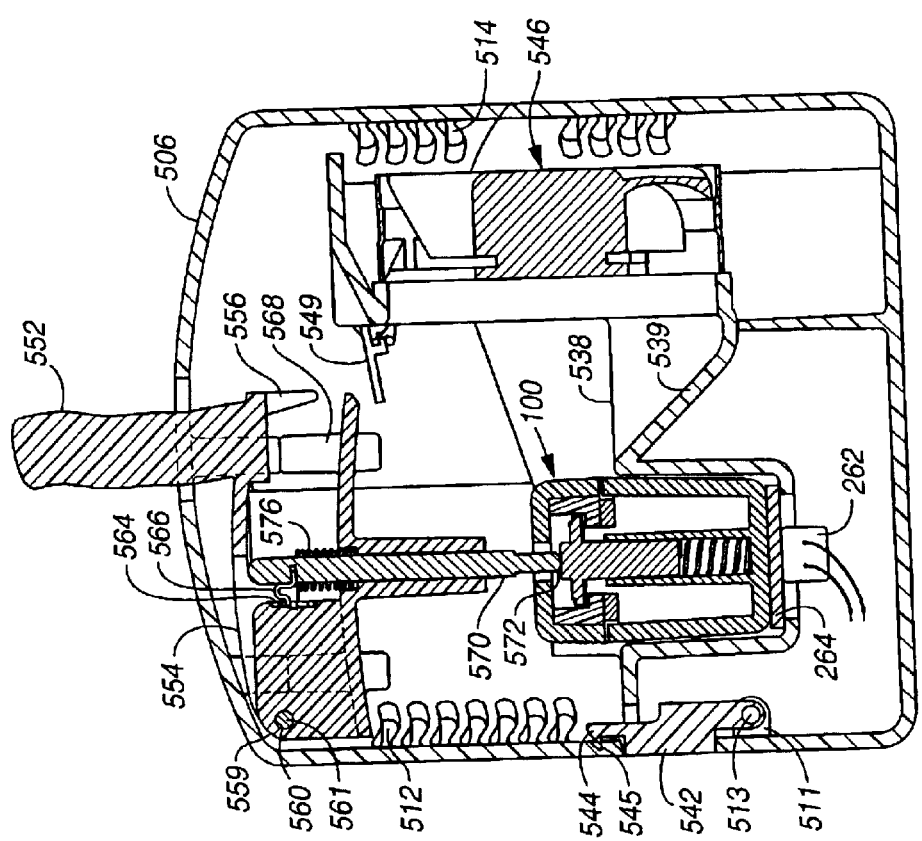
FIG. 19 is a full section view of the scent delivery system of FIG. 15.

As best illustrated in FIG. 19, support body upper surface 538 has a downwardly sloping rear portion 539 for directing the flow of air generated by fan 546 over the top of scent cartridge 100. Upper surface 538 also includes an aperture (not shown) through which heater On/Off control switch 540 is mounted, as well as an indentation 536 along its front edge to prevent interference with latch 542.

An opening 528 is provided extending through a rear vertical wall portion of support body 522 to enable the flow of air generated by fan 546 toward vent openings 512 in upper housing body 502. Furthermore, integral channel 525 is provided for enabling the emission of light from light-emitting diode (LED) 526 into the interior of the system housing. Channel 525 is oriented such that light emitted from LED 526 is directed toward a contact portion 552 of an actuation member 550 (described below) for encouraging the transmission of the emitted light through the contact portion 552. In this manner, the contact portion 552, which is configured to resemble the wick portion of a candle, has the appearance of being lit.

A baffle member, shown generally as reference numeral 558, directs the flow of air generated by fan 546 toward vent openings 512. Baffle member 556 includes bosses 568 through which mechanical fasteners (not shown) are received for fixedly attaching the baffle to the interior surface of topside 506 of upper housing body 502.

A mechanical actuation member, shown generally as reference numeral 550, is pivotally secured to baffle member 558. More particularly, actuation member tines 554 are positioned adjacent opposite sides of baffle wall 559 and pin 561 extends through aligned tine apertures 557 and baffle wall aperture 560 to enable pivotal movement of actuation member 550 thereabout. In this assembled state, contact portion 552 of actuation member 550 extends completely through and beyond aperture 510 in top 506 of upper housing body 502. Primarily for aesthetic purposes, contact portion 552 is preferably configured to have the appearance of a candle wick.

A plunger member having a tip 572 depending downwardly from a main plunger shaft 570 is provided pivotally secured to actuation member 550. Specifically, outwardly extending cylindrical plunger portions 574 are sized for being snap-fittingly received, and subsequently captivated, within rearward extending actuation member hooked portions 555. Plunger tip 572 extends downwardly through baffle channel 562 such that it remains substantially aligned with scent cartridge actuation nub 119 as actuation member 550 pivots with respect to baffle member 558. Similarly, downwardly depending tab portion 556 of actuation member 550 is located such that it is positioned directly above lever 549 of system power switch 548 as upper housing body 502 is closed.

A plunger spring 576 is provided disposed about the outer surface of plunger shaft 570. Upward movement of plunger spring 576 along shaft 570 is restricted by wire member 566. As will be apparent to those skilled in the art, various other means are available for achieving restricted spring movement. By way of example, the upper end of spring 576 can be provided fixedly attached through a plunger shaft aperture (not shown). Alternatively, a thickened plunger shaft portion can be provided adjacent to the upper end of spring 576 to limit upward vertical movement. The spring 576 is sized such that its lower end engages the upper surface of the baffle 558 surrounding channel 562. As a result of the force applied against wire member 566, the spring 576 functions as a means for biasing actuation member 550 upwardly and in a counterclockwise fashion about pin 561.

A rigid plunger wire 566 has a rearward end secured through an aperture in the main plunger body 570 and an opposite forward end captivated within a continuous recessed track 564 in the rearward facing surface of baffle wall 559. The upward bias of plunger shaft 570 effects a corresponding upward bias of the plunger wire 566.

When actuation member 550 is in a non-actuated position, the forward end of wire 566 is captivated at recessed track position 581. In this non-actuated position, plunger tip 572 does not actuate scent cartridge nub 119. Likewise, in this non-actuated position, actuation member tab 556 does not actuate power/fan switch lever 549.

Actuation is accomplished by merely depressing wick-shaped contact portion 552 and then letting go. Upon depressing contact portion 552, the actuation member tab 556 and plunger tip 572 are downwardly displaced to effect corresponding actuation of the scent cartridge nub 119 and the power/fan switch lever 549, respectively. Simultaneously, as spring member 576 becomes increasingly compressed, the forward end of wire member 566 travels along recessed track 564 from position 581 to position 583. Subsequently, upon releasing the pressure on contact portion 552, compressed spring 576 urges the plunger and actuation members upwardly. However, upward movement of wire 566 is restricted as its forward end becomes captivated at the track position denoted 585. In this manner, the scent cartridge nub 119 and power switch lever 549 remain in an actuated orientation, and spring 576 remains partially compressed. Subsequently, upon depressing and then letting go of actuation member contact portion 552, the captivated end of wire 566 returns to track position 581, thereby deactivating the system. In this manner, power supplied to the system through power input means 501 (FIG. 15), as well as actuation of scent emitting cartridge 100, can be controlled by an operator. As will be apparent to those skilled in the art, various alternative means for manually driving a mechanical actuator to effect the aforementioned actuation of the cartridge 100 into an open scent-emitting position could be employed and are contemplated. By way of example, an exterior housing contact button cooperating with a selectively retractable member extending into the housing proximate to cartridge T-member 110, similar to the assemblies commonly incorporated into retractable ball point pens, could be employed for effecting the desired actuation of cartridge 100 between open and closed positions.

During operation, fan 546 draws air into the system through integral vent openings 514 in lower housing body 504, and the air is directed over activated scent cartridge 100 toward vent openings 512 in upper housing body 502, thereby effectively dispersing the desired aroma to the intended surrounding environment. The strength of scent vapors generated within cartridge 100 is increased, by heating the scented fluid contained in the cartridge. As cartridge nub 119 is actuated the generated vapors escape into the housing interior below baffle member 558. Control over the coverage area of the scented vapor to the surrounding external environment can be achieved by controlling the fan speed.

Each of the aforementioned system embodiments incorporate conventional commercially available electronic components and circuitry (not shown) for controlling the various electronic system functions described herein. The incorporation of electronics to enable such control is well known to those skilled in the art and further description is not provided.

As will be apparent to those skilled in the art, various features of the different embodiments of the present invention could be combined without departing from the intended scope of the invention. Furthermore, although certain features have been described with respect to a particular system embodiment, it is contemplated that features from one embodiment could be employed in one or more other system embodiments described herein.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A scent-delivery system, comprising:
    a housing defining a tray-receiving opening and an interior space;
    a tray supported within said housing and slidably movable through said tray-receiving opening between opened and closed positions;
    a plurality of cartridges each containing a scented fluid and supported by said tray;
    mechanical actuating means for actuating each of said plurality of cartridges between a closed position and an open position; and
    blowing means for creating an air flow directed toward said plurality of cartridges.

2. A scent-delivery system as recited in claim 1, further comprising:
    heating means; and
    heat diffusion means interposed between said heating means and said cartridge.

3. A scent-delivery system as recited in claim 2, further comprising timing means for controlling the duration of operation of the system and/or the for pre-selecting a desired starting/stopping time of operation of the system.

4. A scent delivery system as recited in claim 3, further comprising means for electronically controlling the function of said blowing means, said heating means and said timing means.

5. A scent-delivery system as recited in claim 1, wherein said housing has vent openings provided therein for facilitating the communication of a cartridge-emitted scent from the housing interior space to an exterior surrounding environment.

6. A scent-delivery system as recited in claim 5, wherein said blowing mean further comprises a fan attached to a rear portion of said housing and particularly oriented for directing an air flow over top sides of said cartridges and toward the vent openings.

7. A scent-delivery system as recited in claim 1, wherein said cartridge supporting tray further comprises:
   an upper surface generally bounded by a left side, a right side, a rear side and a front face, said upper surface having a plurality of pockets sized and shaped for having said plurality of cartridges seated therein; and
   a sloped area of said upper surface angled downwardly toward the rear side of said tray for directing the flow of air from said blowing means over top sides of said cartridges.

8. A scent-delivery system as recited in claim 7, wherein the sloped area of the upper surface of said tray is positioned directly in front of said blowing means when said tray is in a closed position.

9. A scent-delivery system as recited in claim 1, further comprising electronic means for providing said sliding movement of said cartridge supporting tray.

10. A scent-delivery system as recited in claim 9, wherein said electronic means for providing said sliding movement further comprises an electrically driven pinion attached to an interior surface of said housing and positioned for cooperating with a rack provided along at least one side of said tray.

11. A scent-delivery system as recited in claim 1, wherein said mechanical actuating means further comprises means for driving one or more actuating members downwardly against an upper surface of said scent cartridges.

12. A scent-delivery system as recited in claim 11, wherein said mechanical actuating means further comprises:
   a first horizontally oriented shaft fixedly attached to the interior of said housing;
   a plurality of rocker arms pivotally mounted about said first shaft and each having forward and rear ends; and
   mechanical means for selectively pivoting the forward end of each rocker arm toward a respective cartridge to effect actuation of said cartridge into an open position.

13. A scent-delivery system as recited in claim 12, wherein said mechanical means for selectively pivoting said rocker arms toward said cartridges further comprises:
   a second horizontally oriented shaft having a plurality of cam portions positioned for selectively engaging the respective rear ends of said rocker arms; and
   a motor-driven gear mechanism for imparting rotation to said second shaft.

14. A scent-delivery system as recited in claim 12, further comprising means for pivotally biasing the forward ends of said rocker arms away from said respective cartridges and the rear ends of said rocker arms against said second shaft.

15. A scent-delivery system as recited in claim 14, wherein said biasing means further comprises a torsion spring mounted about said first shaft, the torsion spring having a first end secured to said first shaft and a length extending over and against said rocker arms proximate said rocker arm rear ends.

16. A scent-delivery system, comprising:
   a housing defining a tray-receiving opening and an interior space;
   a tray supported within, said housing and manually slidable through said tray-receiving opening between opened and closed positions;
   a cartridge containing a scented fluid and supported by said tray;
   electromechanical actuating means for actuating said cartridge between a closed position and an open position; and
   blowing means for creating an air flow directed toward said cartridge.

17. A scent-delivery system as recited in claim 16, further comprising:
   heating means; and
   heat diffusion means interposed between said heating means and said cartridge.

18. A scent-delivery system as recited in claim 17, further comprising timing means for controlling the duration of operation of the system and/or the for pre-selecting a desired starting/stopping time of operation of the system.

19. A scent delivery system as recited in claim 18, further comprising means for electronically controlling the function of said blowing means, said heating means and said timing means.

20. A scent-delivery system as recited in claim 16, wherein said electromechanical actuating means further comprises means for driving an actuating member downwardly against an upper surface of said scent cartridge.

21. A scent-delivery system as recited in claim 20, wherein said electromechanical actuating means further comprises:
   a vertically-oriented shaft having a plurality of serrated teeth along its length;
   a gear mechanism configured for cooperating with the serrated teeth to effect vertical movement of said shaft; and
   an electric motor for driving said gear mechanism;
   said shaft positioned over said cartridge for selective actuation of said cartridge between said open and closed positions via said vertical shaft movement.

22. A scent-delivery system as recited in 16, wherein said tray is supported by interior housing guide rails sized and shaped for being slidably received within respective grooves provided along left and right tray sides walls.

23. A scent-delivery system as recited in claim 16, wherein said housing has vent openings provided therein for facilitating the communication of a cartridge-emitted scent from the housing interior space to an exterior surrounding environment.

24. A scent-delivery system as recited in claim 23, wherein said blowing mean further comprises a fan attached to a rear portion of said housing and particularly oriented for directing an air flow over top sides of said cartridges and toward the vent openings.

25. A scent-delivery system as recited in claim 24, further comprising fan speed control means for enabling operator control over the scent coverage area.

26. A scent-delivery system as recited in claim 16, wherein said cartridge supporting tray further comprises:
   an upper surface generally bounded by a left side, a right side, a rear side and a front face, said upper surface having a pocket sized and shaped for having said cartridge seated therein; and a sloped area of said upper surface angled downwardly toward the rear side of said tray for directing the flow of air from said blowing means over top sides of said cartridges.

27. A scent-delivery system as recited in claim 26, wherein the sloped area of the upper surface of said tray is positioned directly in front of said blowing means when said tray is in a closed position.

28. A scent-delivery system as recited in claim 16, further comprising a pressure release mechanism for selectively imparting a force against said cartridge-supporting tray to effect movement of said tray toward an open position.

29. A scent-delivery system, comprising:
- a housing having upper and lower housing bodies defining an interior housing space;
- a support structure contained within said interior space and supported within the lower housing body;
- a scent-emitting cartridge supported by said support structure;
- a blowing means attached to said internal support structure; and
- manually-driven means for mechanically actuating the scent-emitting cartridge between open and closed positions when said upper housing body is in a closed position.

30. A scent-delivery system as recited in claim 29, wherein said system further comprises an internal power supply switch and said manually-driven means for mechanically actuating the scent-emitting cartridge includes structure for mechanically actuating said power supply switch.

31. A scent-delivery system as recited in claim 29, wherein said upper housing body is pivotally attached to said support structure.

32. A scent-delivery system as recited in claim 29, wherein said scent-emitting cartridge is supported within a pocket provided in said support structure.

33. A scent-delivery system as recited in claim 32, wherein said support structure pocket has an opening provided through a lower surface thereof and said system further comprises:
- a heating means extending upwardly at least partially through the lower surface opening of said pocket; and
- heat diffusion means interposed between said heating means and a bottom surface of said cartridge.

34. A scent-delivery system as recited in claim 29, further comprising heating means for heating said cartridge.

35. A scent-delivery system as recited in claim 29, wherein said manually-driven mechanical actuation means drives an actuating member downward against an upper surface of said scent cartridge.

36. A scent-delivery system as recited in claim 35, wherein said mechanical actuation means further comprises:
- a baffle member fixedly secured to an interior surface of said housing;
- a unitary actuation member pivotally attached to said baffle member and having a contact portion extending through an aperture in said housing; and
- a plunger assembly pivotally supported by said actuation member and having a plunger tip extending through an aperture in said baffle member and positioned for actuating said cartridge between open and closed positions.

37. A scent-delivery system as recited in claim 36, wherein said mechanical actuation means is configured for alternating displacement of said actuating member between raised and lowered positions through successive pressure contact with said contact portion.

38. A scent-delivery system having the configuration and form of an electronic candle, comprising:
- a housing having upper and lower cooperating housing bodies defining an interior space and configured to have the form and appearance of a candle body when said housing is in a closed position, a topside of said upper housing body having an aperture extending therethrough;
- an actuation member supported within the housing interior space and having a contact portion extending upwardly through the aperture in said upper housing, the contact portion configured to have the form and appearance of a candle wick;
- a cartridge containing a scented oil supported within the housing interior space;
- means for enabling selective actuation of said cartridge between opened and closed positions via manual depression of said contact portion, said selective actuation means attached at a first end to said actuation member and having a second end positioned and configured for effecting said cartridge actuation; and
- means for controllably communicating a scented oil aroma from said cartridge to an exterior environment.

39. A scent-delivery system as recited in claim 38 wherein the contact portion of said actuation member is constructed for enabling transmission of light therethrough, said system further comprising a light source communicating light to said contact portion for giving the contact portion the appearance of a candle flame.

40. A scent-delivery system, comprising:
- a main housing body;
- a housing lid cooperating with said main housing body to define an interior space;
- a scent-emitting cartridge supported within said interior space;
- a blowing means for communicating an air flow into said interior space; and
- a downward moving actuation member for manually actuating said scent-emitting cartridge between opened and closed positions, said actuation member having the form of a protuberance depending downwardly from an interior surface of said housing lid and positioned for manually actuating said cartridge toward an open position when said lid is fully attached to said main housing body.

41. A scent-delivery system, comprising:
- a main housing body;
- a housing lid cooperating with said main housing body to define an interior space;
- a scent-emitting cartridge supported within said interior space;
- a blowing means for communicating an air flow into said interior space;
- means for manually actuating said scent-emitting cartridge between opened and closed positions;
- heating means; and
- heat diffusion means interposed between said heating means and said cartridge.

42. A scent-delivery system as recited in claim 41, wherein said blowing means comprises a fan and said system further comprises an electronic switch for controlling power to said fan and said heating means.

* * * * *